United States Patent [19]

Reich et al.

[11] 4,199,013

[45] Apr. 22, 1980

[54] LIQUID SAMPLE ASPIRATING AND/OR DISPENSING SYSTEM

[75] Inventors: Andrew R. Reich; Leroy J. Everett, both of Glen Ellyn, Ill.

[73] Assignee: Packard Instrument Company, Inc., Downers Grove, Ill.

[21] Appl. No.: 783,795

[22] Filed: Apr. 1, 1977

[51] Int. Cl.² .................... B65B 43/42; B67C 3/00; B67D 5/52
[52] U.S. Cl. ................................ 141/130; 141/136; 141/138; 222/135
[58] Field of Search ............... 141/130, 135, 136, 137, 141/138, 90; 23/259; 222/135, 137

[56] References Cited

U.S. PATENT DOCUMENTS

| | | | |
|---|---|---|---|
| 3,401,839 | 9/1968 | Christie | 222/137 |
| 3,525,592 | 8/1970 | Buckley | 222/135 |
| 3,753,657 | 8/1973 | Downing et al. | 141/130 |
| 3,768,526 | 10/1973 | Sanz et al. | 141/130 |
| 3,926,229 | 12/1975 | Scholle | 141/90 |
| 3,963,148 | 6/1976 | Proni et al. | 23/259 |

*Primary Examiner*—Steven L. Stephan
*Attorney, Agent, or Firm*—Leydig, Voit, Osann, Mayer & Holt

[57] ABSTRACT

A pipetting system for dispensing multiple liquids into a single receptacle includes a plurality of liquid reservoirs, a plurality of syringes for aspirating preselected quantities of liquids from the reservoirs, and a common dispensing head connected to all the syringes for simultaneously receiving the preselected quantities of liquids from a plurality of the syringes and simultaneously dispensing the liquids into the reservoir. The system also includes means for simultaneously aspirating the preselected quantities of liquids from the reservoirs into the syringes. In addition, the system includes aspirating means for withdrawing a liquid sample from a container into the dispensing head at an aspirating position, means for storing the aspirated sample while the dispensing head is moved from the aspirating position to a dispensing position, and means for dispensing the aspirated sample to the dispensing head simultaneously with the dispensing of the preselected quantities of other liquids. The dispensing/aspirating head is mounted for vertical movement in both the dispensing and aspirating positions to permit the lower end of the head to be lowered into both the aspirating container and the dispensing receptacle, and means are provided for automatically stopping the downward movement of the head at different preselected elevations in the dispensing and aspirating positions, and means for adjusting those preselected elevations.

12 Claims, 14 Drawing Figures

U.S. Patent Apr. 22, 1980 4,199,013
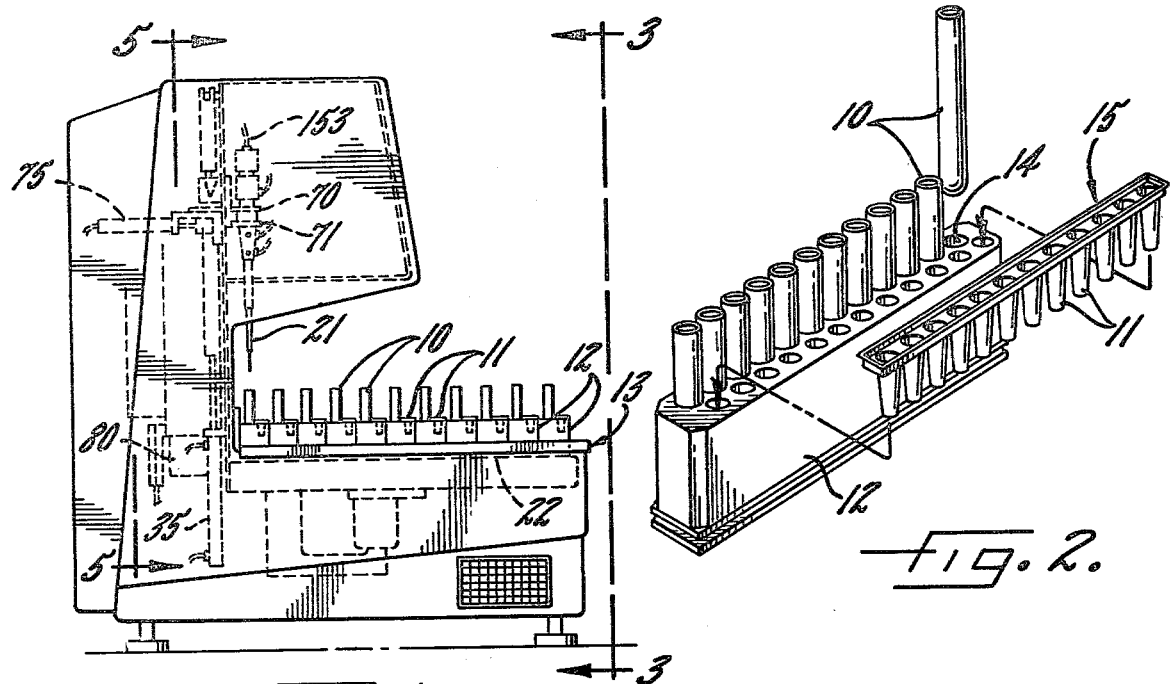
Fig. 1.
Fig. 2.
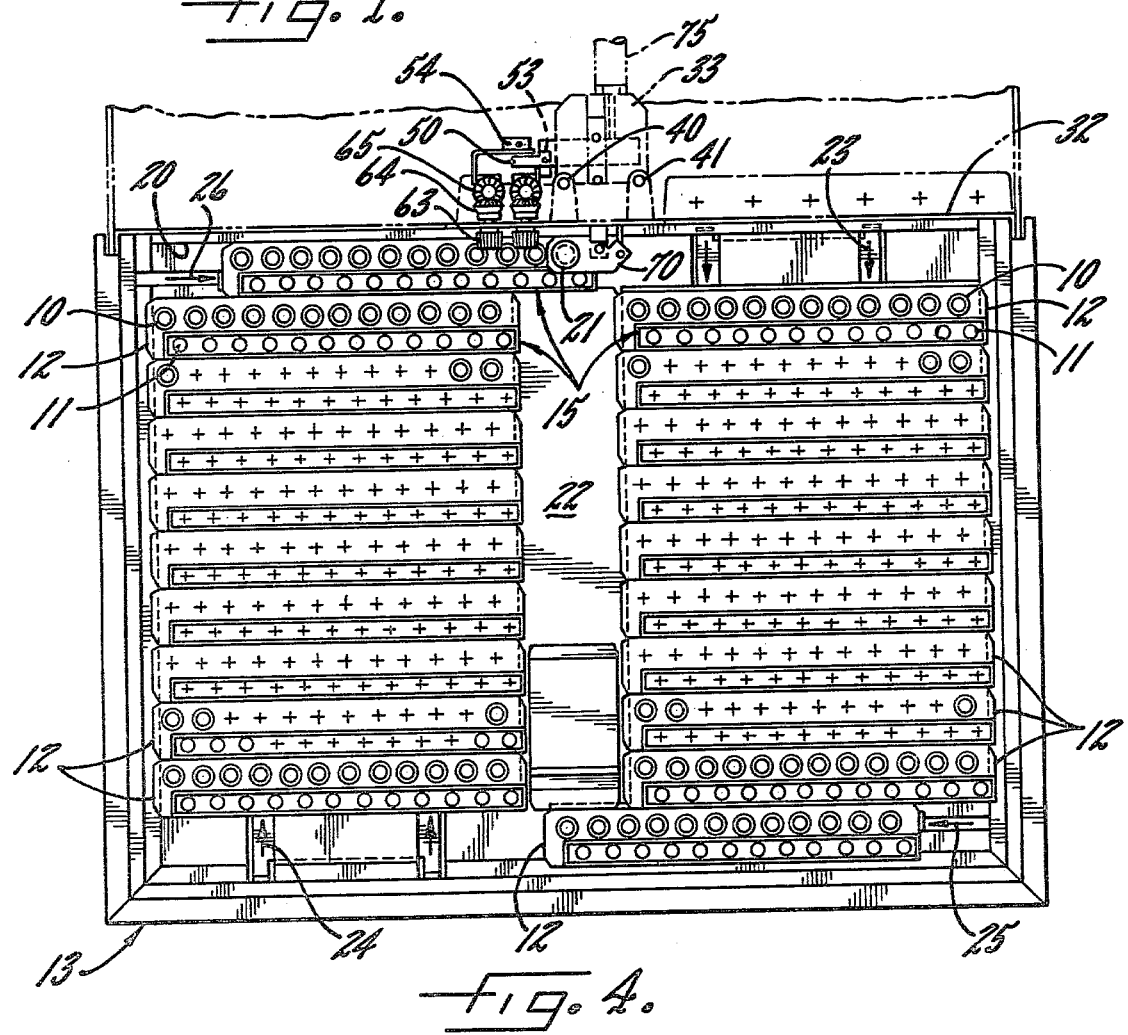
Fig. 4.

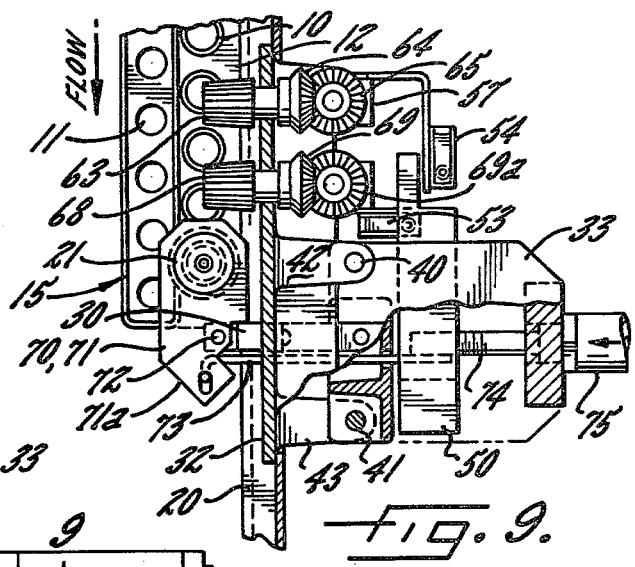
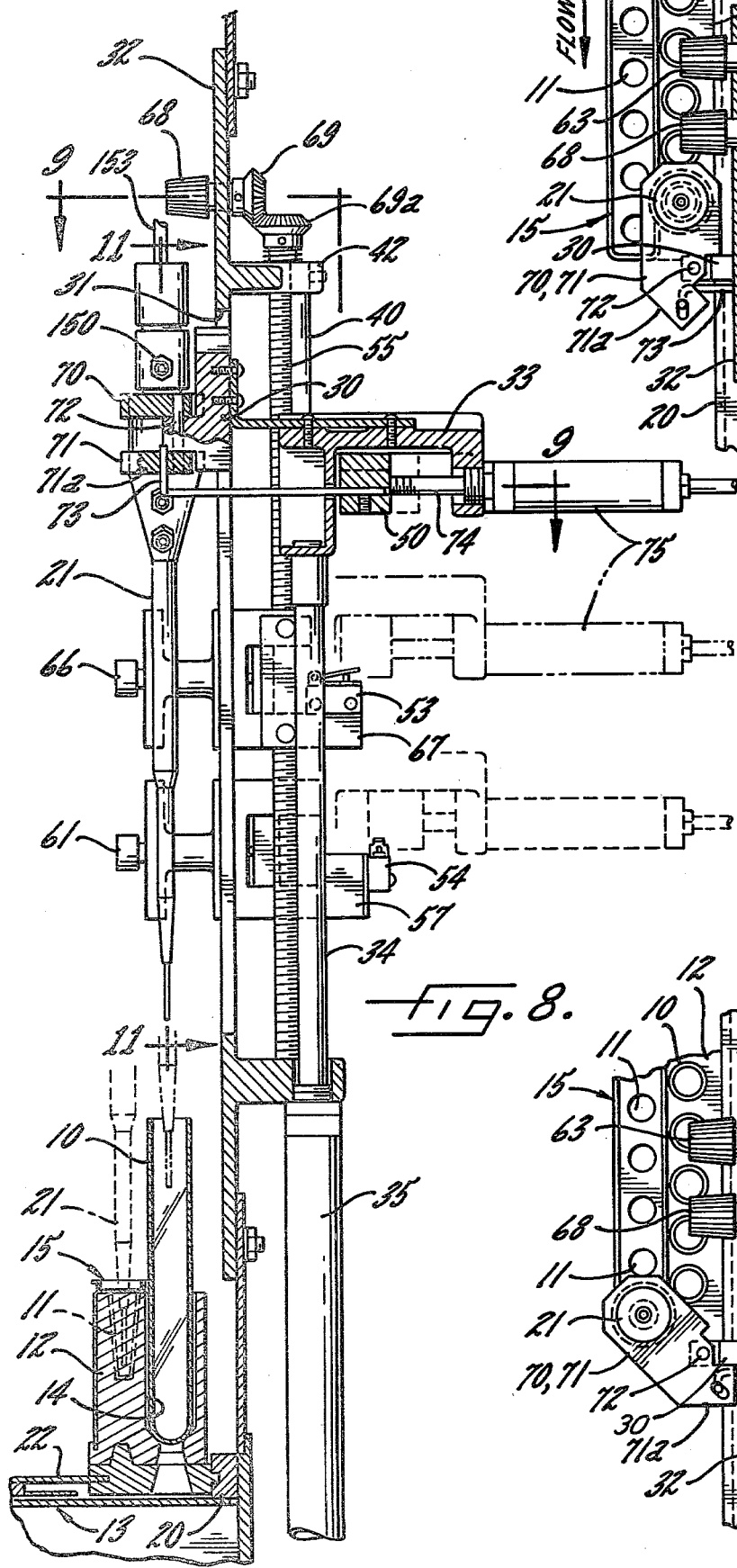
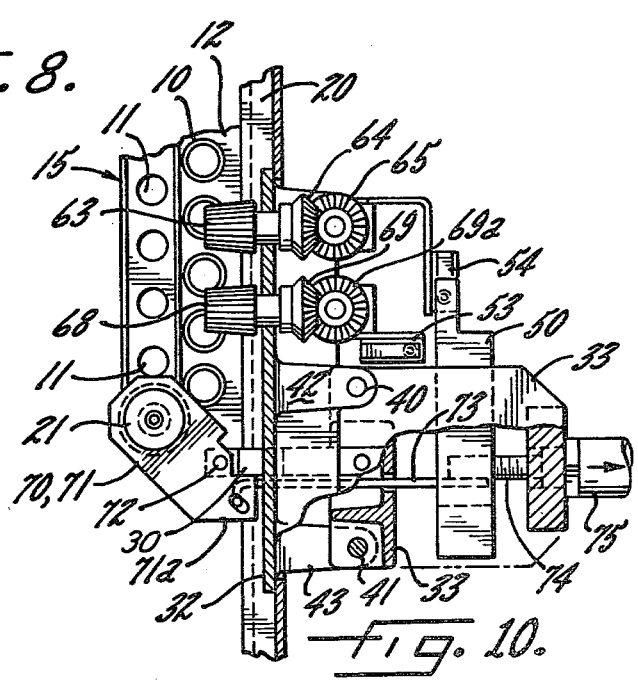

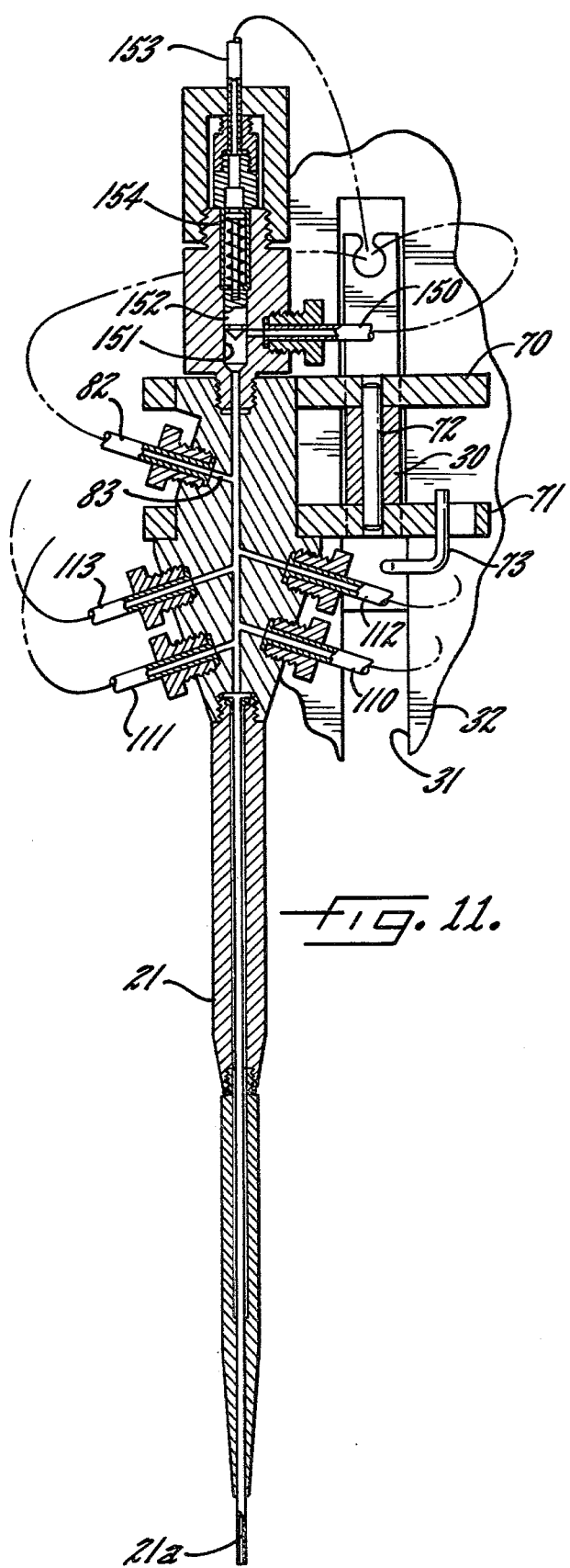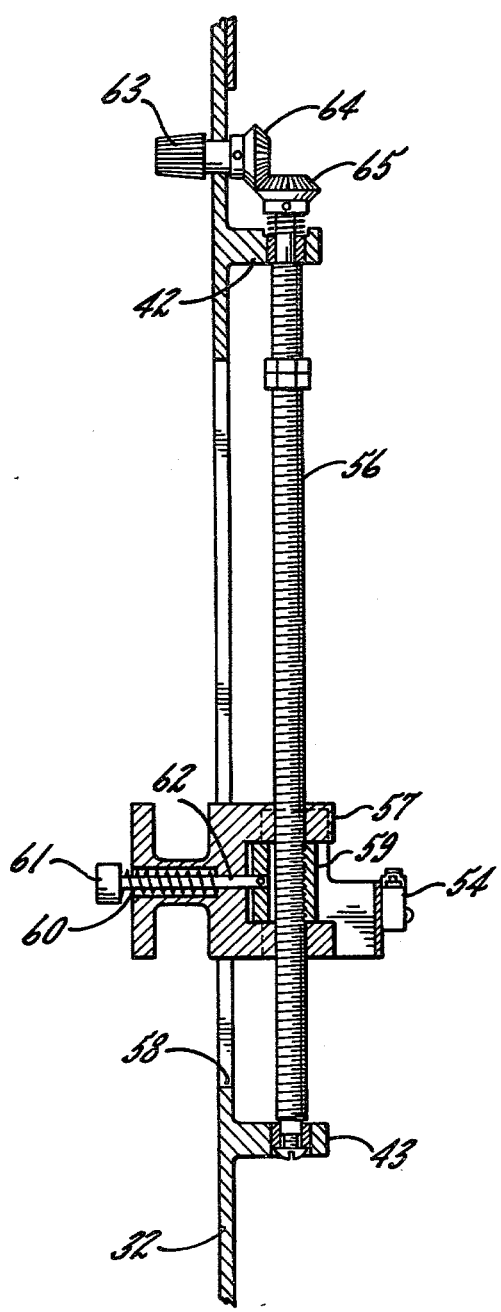

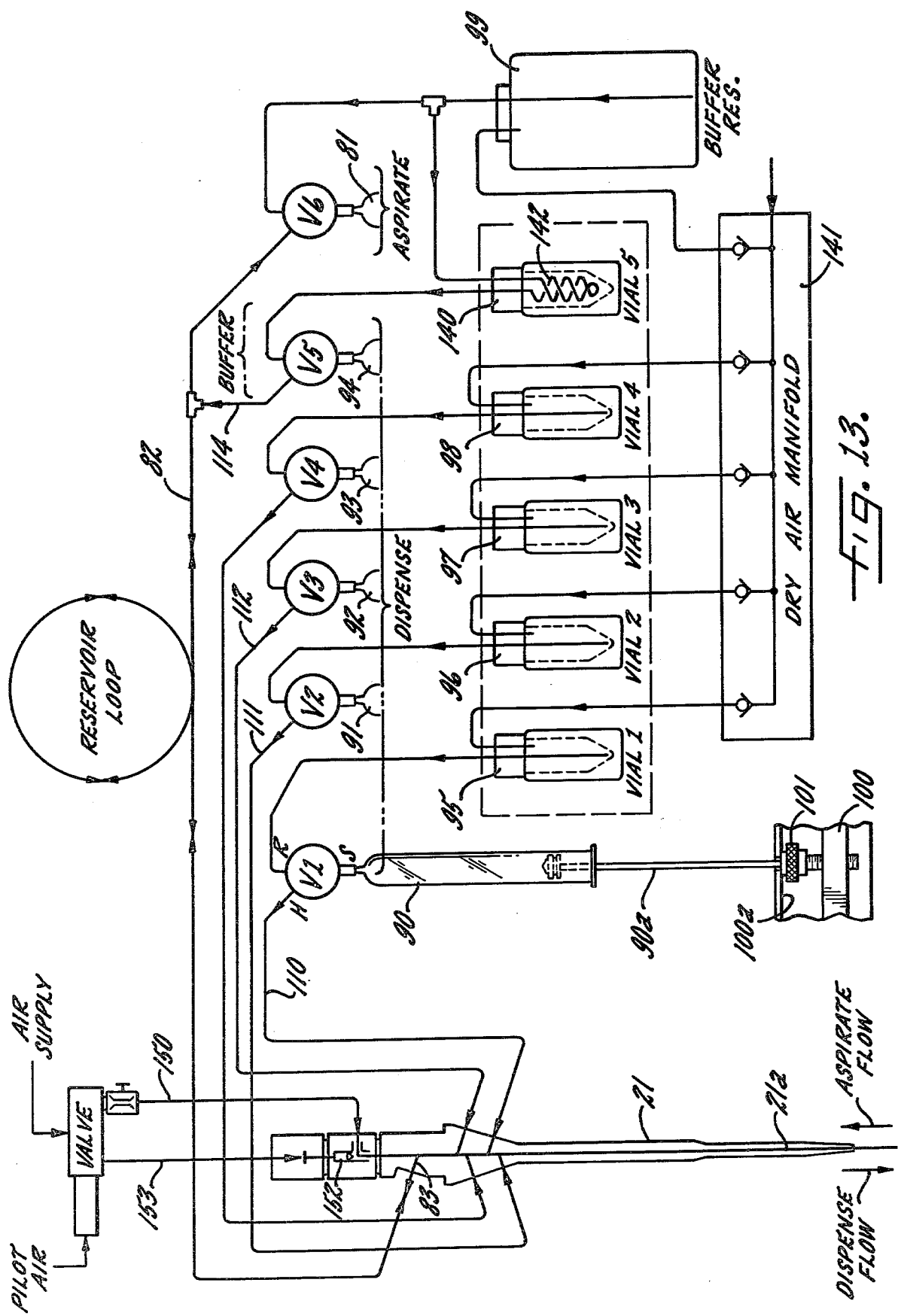

LIQUID SAMPLE ASPIRATING AND/OR DISPENSING SYSTEM

DESCRIPTION OF THE INVENTION

The present invention relates generally to pipetting and aspirating systems and, more particularly, to such systems which are capable of dispensing multiple reagents into a common receptacle. This invention is particularly useful in the preparation of samples for use in such microchemical techniques as electrolyte determinations, enzyme activities, and various radiochemical assay procedures.

It is a principal object of this invention to provide an improved pipetting system which is capable of dispensing multiple reagents quickly and accurately.

It is another important object of the invention to provide such an improved pipetting system which is also capable of aspirating liquid samples from outside the system and then dispensing the aspirated samples along with multiple reagents stored in the pipetting system.

A further object of the present invention is to provide such an improved pipetting system which ensures that each aspirated sample is completely discharged from the pipetting system before aspiration of the next sample.

A still further object of the invention is to provide such an improved pipetting system which ensures the aspiration and dispensing of accurate preselected volumes of the various liquids, and which permits the preselected volumes to be easily adjusted.

Yet another object of the invention is to provide such an improved pipetting and aspirating system which permits automatic control of the vertical travel of the dispensing head to minimize liquid carry-over between receptacles, to avoid liquid splashing within the receptacle, and to accommodate different sizes of sample tubes.

Still another object of one specific aspect of the invention is to provide such a system which prevents aspirated samples from mixing with or diffusing into the internal liquid that effects the aspiration.

Other objects and advantages of the invention will be apparent from the following detailed description and the accompanying drawings, in which:

FIG. 1 is a side elevation of a benchtop pipetting and aspirating instrument embodying the present invention, in conjunction with a multiple sample storage and indexing system for transferring successive sample containers through the system in a multiplicity of cassettes;

FIG. 2 is an enlarged perspective view of one of the multiple sample cassettes removed from the instrument of FIG. 1, and with certain of the sample containers shown in exploded positions;

FIG. 4 is a top plan view of the front portion of the instrument of FIGS. 1 and 3, taken generally along line 4—4 in FIG. 3;

FIG. 8 is a section taken generally along line 8—8 in FIG. 5, with the dispensing/aspirating head shown in its raised position in solid lines and in two different lowered positions in broken lines;

FIG. 9 is a section taken generally along line 9—9 in FIG. 8 with the dispensing/aspirating head in its inboard position;

FIG. 10 is the same sectional view shown in FIG. 9 but with the dispensing/aspirating head in its outboard position;

FIG. 11 is an enlarged section taken generally aling line 11—11 in FIG. 8;

FIG. 12 is a section taken generally aling line 12—12 in FIG. 5;

FIG. 13 is a schematic diagram of the liquid flow system embodied in the instrument of FIGS. 1 through 12.

Figure 3:
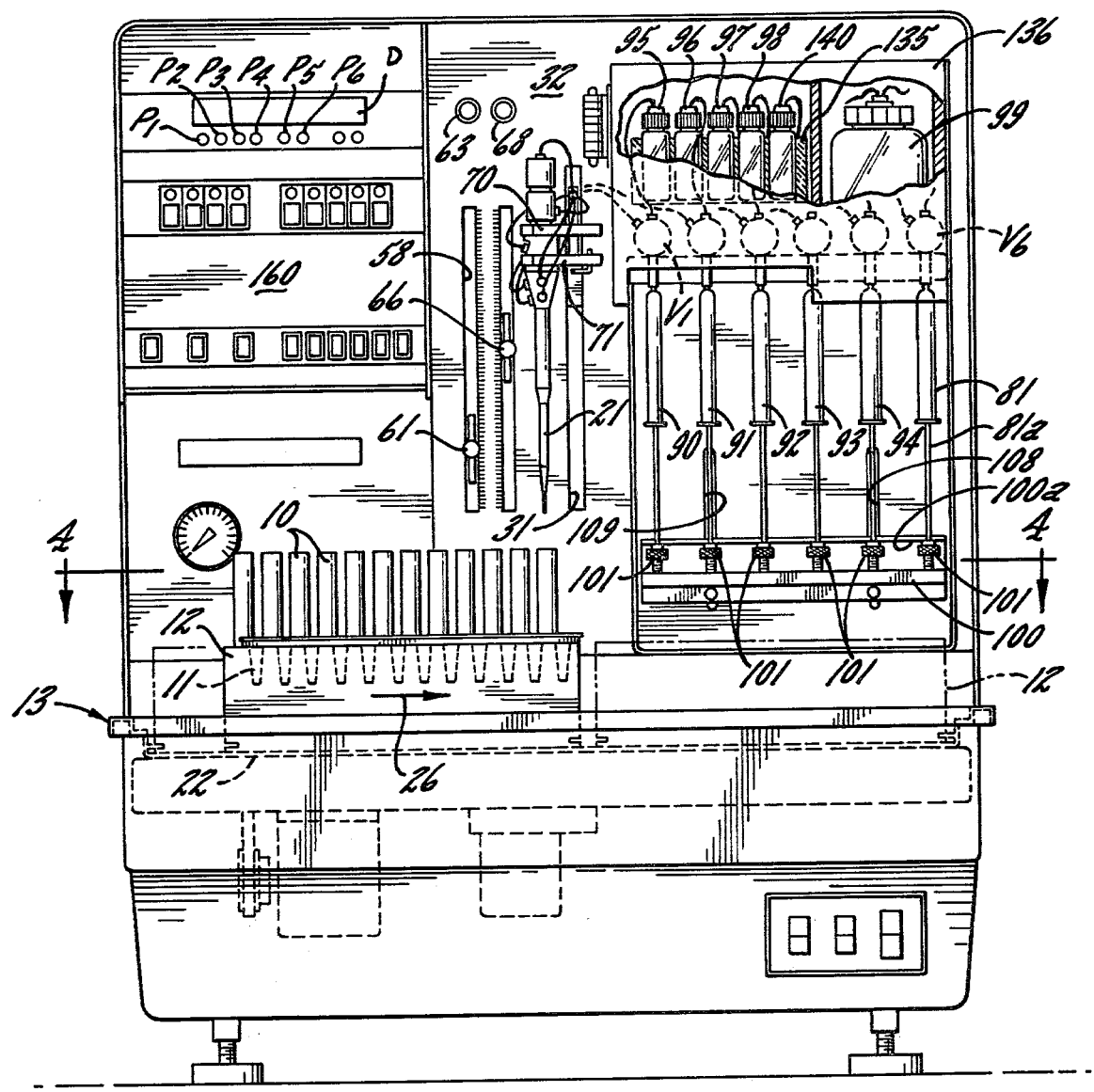
FIG. 3 is an enlarged front elevation of the pipetting and aspirating instrument shown in FIG. 1, with a fragment of the door in the upper right-hand corner of the instrument broken away to show the internal structure.

While the invention will be described in connection with certain preferred embodiments, it is to be understood that the invention is not limited to these particular embodiments. On the contrary, it is intended to cover all alternatives, modifications and equivalents as may be included within the spirit and scope of the invention as expressed in the appended claims.

Turning now to the drawings and referring first to FIGS. 1 through 4, there is shown a benchtop sample preparation instrument which is capable of dispensing multiple reagents into, and aspirating liquid specimens from, a multiplicity of sample tubes 10 and specimen cups 11 carried in cassettes 12 on a stage 13 at the front of the instrument. Each of the cassettes 12 holds twelve of the sample tubes 10 resting loosely in compartments 14 in the cassette, and twelve specimen cups 11 formed as integral parts of a unitary specimen strip 15. Of course, separate specimen cups could be employed if desired. The tubes 10 may be of different heights and diameters if desired, and are preferably in staggered relationship to the specimen cups 11.

The illustrative instrument has a variety of different uses in the preparation of samples for microchemical assays, such as preparation of samples by dilution to specified concentration levels, adding the necessary reagents to be used in the sample assays, or separating liquid and solid phases of the samples after precipitation. The instrument is particularly useful in radioimmunoassay in which an antiserum containing an antibody with a specific reactivity and specificity is mixed with a predetermined amount of radionuclide-labeled antigen and a sample of a patient's serum containing the antigen to be measured. In this mixture the antibody reacts with both the labeled and the unlabeled antigen, forming an antigen-antibody complex. After an incubation period, the complexed antigens and antibodies are separated from the uncomplexed antigens and antibodies, such as by centrifuging to cause the complexed material to precipitate out. The uncomplexed material is then decanted out of the reaction container so that the radioactivity contained in the complexed and uncomplexed fractions can be measured. The instrument provided by the present invention is useful in both the sample preparation and the separation steps of this assay technique.

To permit the addition and removal of liquids to and from the multiplicity of sample tubes 10 and specimen cups 11 stored on the stage 13, successive cassettes 12 are indexed along a track 20 at the rear of the stage 13 to bring successive tubes 10 into register with a dispensing and aspirating head 21 having a vertical bore 21a. As will be described in more detail below, the head 21 can be pivoted between inboard and outboard positions for alignment with either a sample tube 10 or a specimen cup 11. In the illustrative embodiment, two rows of ten cassettes each are mounted on a tray 22 for indexing movement along two y-direction paths 23 and 24 and two x-direction paths 25 and 26. As can be seen most clearly in FIG. 4, the two y-direction paths 23 and 24 extend parallel to the sides of the tray 22, perpendicular to the rows of tubes 10 and cups 11 in the various cassettes 12, while the two x-direction paths 25 and 26 extend along the front and rear of the tray, parallel to the rows of tubes and cups in the cassettes. The x and y paths thus form a closed loop extending around the perimeter of the tray 22, with the rear x-direction path 26 carrying the cassettes under the dispensing/aspirating head 21.

To permit the tip of the dispensing/aspirating head 21 to be lowered into the sample tubes 10 and specimen cups 11, the head 21 is carried on a guide block 30 riding in an elongated vertical slot 31 formed in the front panel 32 of the instrument. The guide block 30 in turn is carried on a bracket assembly 33 mounted on the upper end of a cylinder rod 34 behind the panel 32. This rod 34 is part of a pneumatic drive cylinder 35 which is mounted on the panel 32 and is automatically actuated to raise and lower the head 21. Thus, it can be seen than when the pneumatic cylinder 35 is actuated to advance the rod 34, the dispensing/aspirating head 21 is raised; and conversely, when the cylinder 35 is actuated to retract the rod 34, the head 21 is lowered. Although it is necessary to remove the upward force from the cylinder 35 before the head 21 can descend, it should be noted that downward movement of the head 21 is by gravity. Thus, the descent of the head 21 can be stopped at any desired position by means of a mechanical stop without the need to de-activate the cylinder 35.

Figure 5:
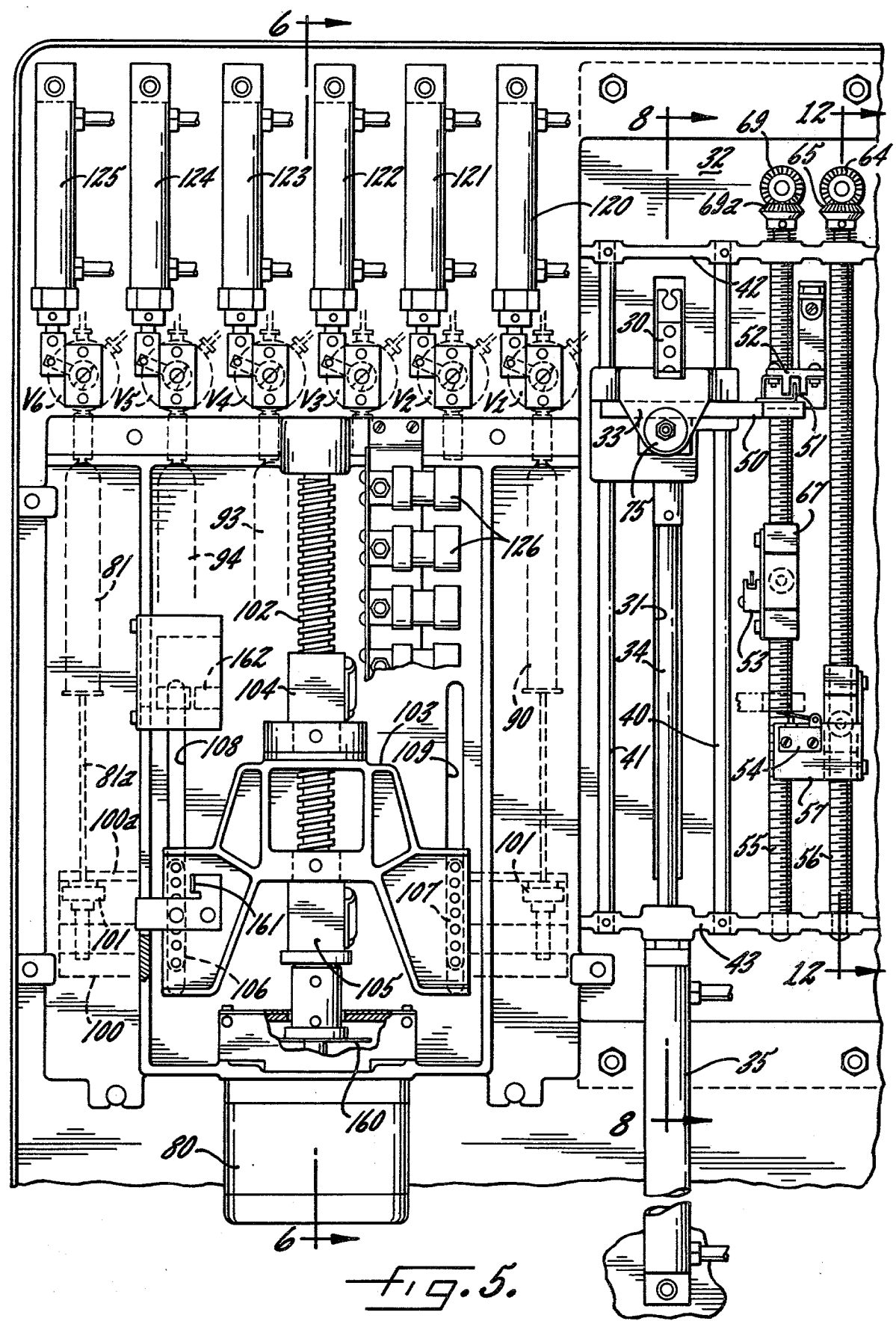
FIG. 5 is an enlarged fragmentary section taken generally along line 5—5 in FIG. 1.
Figure 6:
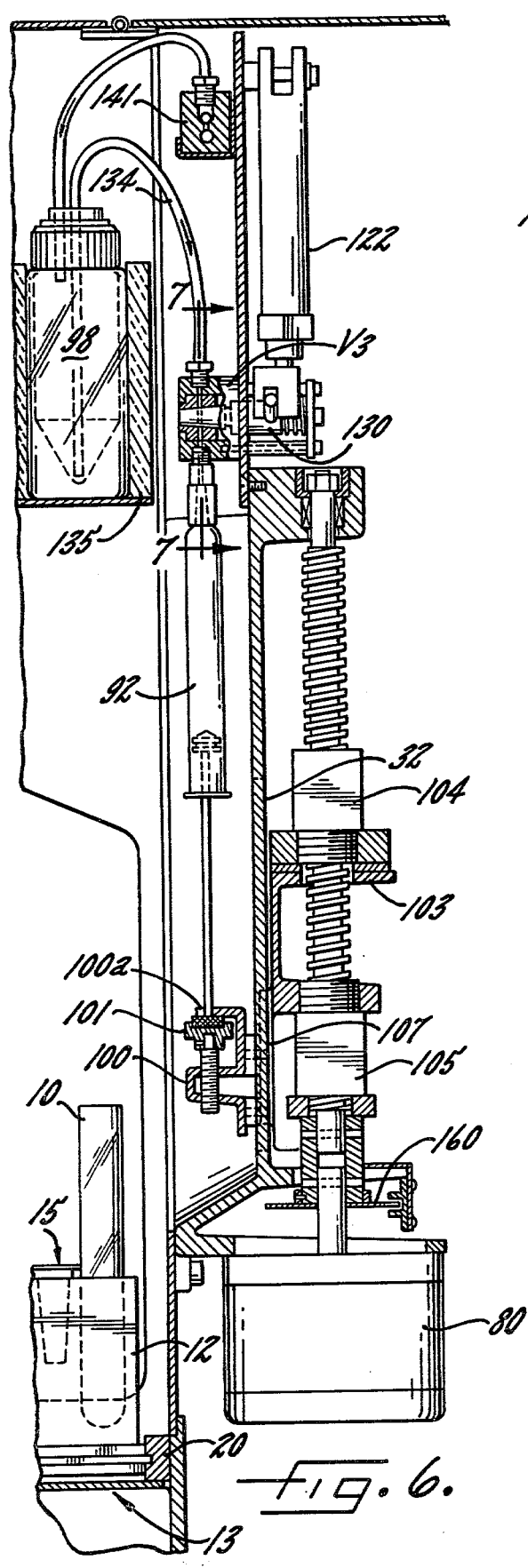
FIG. 6 is a section taken generally along line 6—6 in FIG. 5.

For the purpose of stabilizing the bracket assembly 33 and the guide block 30 and dispensing/aspirating head 21 carried thereby during their vertical travel, the bracket assembly 33 rides on a pair of spaced guide rods 40 and 41 (FIG. 5) located on opposite sides of the cylinder rod 34 behind the panel 32. The top and bottom ends of these guide rods 40 and 41 are secured within complementary bosses projecting from a pair of rigid flanges 42 and 43 formed as integral parts of the panel 32. The lower flange 43 also forms a boss which supports the upper end of the drive cylinder 35.

In accordance with one aspect of the present invention, means are provided for automatically stopping the downward movement of the dispensing/aspirating head 21 at a preselected elevation which is adjustable so that the tip of the head can be stopped at any desired position relative to the liquid level within the sample tubes 10 or the specimen cups 11. For example, when the head is lowered into one of the tubes or cups to aspirate a sample therefrom, the tip of the head can be positioned to minimize the immersion depth of the tip and the amount of liquid carry-over from sample to sample and thereby increase the accuracy of the analyses, to ensure against the aspiration of air along with the liquid sample, and/or to ensure that only the desired fraction of a multilayer sample is aspirated. When the head is operated in a dispensing mode, the top of the head can be positioned to minimize the amount of liquid splashed onto the upper tube walls above the liquid level therein.

Thus, to control the vertical travel of the head 21, the bracket assembly 33 includes a laterally extending actuator arm 50 which actuates a sensor at the upper end of the vertical travel of the head 21 to control operation of the drive cylinder 35 via a solenoid-operated air valve (not shown). More specifically, the actuator arm 50 includes an upturned flange 51 (FIG. 5) which interrupts the light beam in a photo-electric sensor 52 when the head 21 reaches the upper end of its vertical travel (which is a constant position in the illustrative embodiment). The lower terminus of each cycle of vertical travel of the head 21 is determined by the location of one of a pair of limit switches 53 and 54, depending on the angular position of the dispenser head 21 in any given cycle. That is, when the head 21 is in its inboard position in alignment with one of the sample tubes 10, as illustrated in FIG. 1, the actuator arm 50 is aligned with the limit switch 53 so that the downward movement of the head 21 is terminated when the bottom of the actuator arm 50 engages the limit switch 53. When the dispenser head 21 is pivoted to its outboard position in alignment with one of the specimen cups 11, as illustrated in FIG. 10, the actuator arm 50 is aligned with the second limit switch 54 so that downward movement of the head 21 is terminated when the bottom of the actuator arm 50 engages the limit switch 54. It should be understood that the limit siwtches 53 and 54 function as mechanical stops to terminate downward movement of the head 21, while at the same time generating electrical signals which can be used to initiate the next function in the system, e.g., an aspirating or dispensing operation.

To permit adjustment of the lower terminus of travel of the head 21, the two limit switches 53 and 54 are mounted on threaded shafts 55 and 56, and means are provided for both coarse and fine adjustments of the positions of the limit switches 53 and 54 on their respective shafts. As shown most clearly, in FIG. 12, the coarse adjustment for the limit switch 54 is effected by disengaging its mounting block 57 from the threaded shaft 56 so that the mounting block and the switch 54 can be manually moved along the length of the shaft 56. This manual movement of the mounting block 57 is guided by a forward extension of the guiding block 57 which rides in a vertical slot 58 formed in the front panel 32 of the instrument. Telescoped within this mounting block 57 is a slidable insert 59 which is normally held in threaded engagement with the shaft 56 by means of a spring 60 urging a knob 61 and its shaft 62 (connected to the insert 59) through the mounting block 57. To effect a coarse adjustment in the position of the limit switch 54, the knob 61 is depressed against the bias of the spring 60, thereby releasing the insert 59 from its threaded engagement with the shaft 56 so that the mounting block 57 can be freely moved along the length of the shaft 56.

After the mounting block 57 has been moved to the approximate desired position for the limit switch 54, the switch position can be finely adjusted by turning a knob 63 attached to a bevel gear 64 meshing with a complementary bevel gear 65 secured to the top end of the shaft 56. This knob 63 is turned after the knob 61 has been released to restore the threaded engagement between the insert 59 and the threaded shaft 56, so that turning the bevel gears 64, 65 results in rotation of the shaft 56 to move the switch 54 slowly along the shaft 56 until the switch 54 reaches precisely the desired position.

The mechanism for adjusting the position of the second limit switch 53 is exactly the same as that just described for the switch 54. Thus, to effect a coarse adjustment in the position of the limit switch 53, a knob 66 is depressed to release a mounting block 67 from the shaft 55 so that the mounting block 67 can be freely moved along the length of the shaft 55. After the mounting block 67 has been moved to the approximate desired position for the limit switch 53, the switch position can be fully adjusted by turning a knob 68 attached to a bevel gear 69 meshing with a complementary bevel gear 69a secured to the top of the shaft 55. This knob 68 is turned after the knob 66 has been released to restore the threaded engagement between the mounting block 67 and the threaded shaft 55, so that turning the bevel gears 69, 69a results in rotation of the shaft 55 to move the switch 53 slowly along the shaft until the switch reaches precisely the desired position.

For the purpose of effecting pivotal movement of the dispensing/aspirating head 21 from the inboard position where the head is aligned with a sample tube 10 to the outboard position where the head is aligned with a specimen cup 11, the head 21 is mounted on the guide block 30 via a pair of horizontal links 70 and 71. These links 70 and 71 are both pivoted on the guide block 30 by means of a common shaft 72. To pivot the links 70 and 71, and thus the head 21, about the shaft 72, a drive rod 73 is connected from a lateral projection 71a of the lower link 71 to a cylinder rod 74 of a cylinder 75 mounted on the back of the bracket assembly 33. Consequently, when the cylinder rod 74 is advanced, as illustrated in FIG. 9, the head 21 is pivoted to its inboard position in alignment with one of the sample tubes 10. When the cylinder rod 74 is retracted, as illustrated in FIG. 10, the head 21 is pivoted to its outboard position in alignment with one of the specimen cups 11. As can be seen in FIGS. 8, 9 and 10, the actuator arm 50 is also connected to the cylinder rod 74 so that it is advanced and retracted along with the drive rod 73, thereby positioning the actuator arm in alignment with either the limit switch 53 (when the head 21 is in its inboard position as shown in FIG. 9) or the limit switch 54 (when the head is in its outboard position as shown in FIG. 10.

It can be seen from the description thus far that the dispensing/aspirating head 21 can be moved to either of two angular positions, depending on whether it is desired to dispense or aspirate liquid to or from a sample tube 10 or a specimen cup 11. In both angular positions, the head 21 can be raised and lowered, with the depth of penetration of the tip of the head into the tube 10 or cup 11 being adjustably controlled by the vertical positions of the limit switches 53 and 54.

When it is desired to aspirate a liquid sample into the head 21, a drive motor 80 is energized to retract the plunger 81a of an aspirating syringe 91 connected via valve V6 to a flexible tube 82 leading to a port 83 in the head 21. The syringe 81 and the tube 82 are pre-filled with a buffer liquid (e.g., phosphate buffered saline) so that retraction of the sryinge plunger 81a draws liquid from the specimen cup 11 upwardly into the head 21 due to the vacuum produced by withdrawal of liquid from the tube 82. Depending on the quantity of liquid sample that is aspirated, the aspirated liquid may fill not only the longitudinal passageway within the head 21 but also a portion of the tube 82. To ensure that the aspirated liquid sample is never drawn all the way back through the tube 82 into the valve V6 leading to the aspirating syringe 81, a reservoir loop 82a is formed in the flexible tube 82 so as to provide sufficient storage capacity for retaining the maximum volume of aspirated liquid sample within the tube 82.

At the same time that the plunger for the aspirating syringe 81 is retracted, the plungers of five parallel syringe 90, 91, 92, 93, and 94 are also retracted to withdraw reagents from four reservoir vials 95, 96, 97 and 98 into syringes 90-93 and from a buffer liquid reservoir 99 into syringe 94. Thus, reagents are aspirated from the four vials 95-98 into the syringes 90-93, and buffer liquid is aspirated from the reservoir 99 into the syringe 94, at the same time that the liquid sample is aspirated from the specimen cup 11 into the head 21 and tube 82. This simultaneous aspiration by all six syringes 81 and 90-94 is effected by a common drive bar 100 connected to the drive motor 80. This drive bar 100 captures a knurled knob on the end of each syringe plunger between a flange 100a of the drive bar and six threaded knobs 101 which can be threaded upwardly to grip the knurled knobs tightly against the flange 100a. The plungers are initially inserted into the flange 100a through openended slots in the front edge thereof, and are then clamped to the flange by the knobs 101. Consequently, when the drive motor 80 is energized to lower the drive bar 100, it retracts all six syringe plungers simultaneously; and conversely, when the drive motor 80 is reversed to raise the drive bar 100, is simultaneously advances all six syringe plungers.

The interconnection between the drive motor 80 and the drive bar 100 comprises a threaded shaft 102 driven by the motor and coupled to a bracket 103 by ball nuts 104 and 105. The bracket 103 carries the drive bar 100 so that when the motor 80 is energized in one direction the drive bar 100 is raised, and when the motor 80 is energized in the other direction the drive bar 100 is lowered. For the purpose of guiding the drive bar 100 during its vertical travel, the bracket 103 carries a pair of guide members 106 and 107 which ride in a pair of complementary slots 108 and 109 formed in the panel 32. These guide members 106 and 107 provide lateral stability to the drive bar 100 to ensure that the bar is maintained in a horizontal position to advance and retract the six syringe plungers uniformly.

In order to aspirate liquid into the six syringes 81 and 90-94, six valves V1-V6 connected thereto must be positioned to connect the syringes to their respective liquid reservoirs. Each of these six valves V1-V6 has two positions: a "reservoir" position in which the valve connects its syringe to the corresponding liquid reservoir, and a "head" position in which the valve connects the syringe to the dispensing/aspirating head 21 via flexible tubes 110-114 and the sample aspirating tube 82. Each of the tubes 110-113 leads to a separate port in the head 21, while the tube 114 merges with the tube 82 leading to the port 83 in the head. The valves V1-V6 are actuated by six pneumatic cylinders 120-125 (FIG. 5), which in turn are controlled by six solenoid-operated air valves 126.

Figure 7:
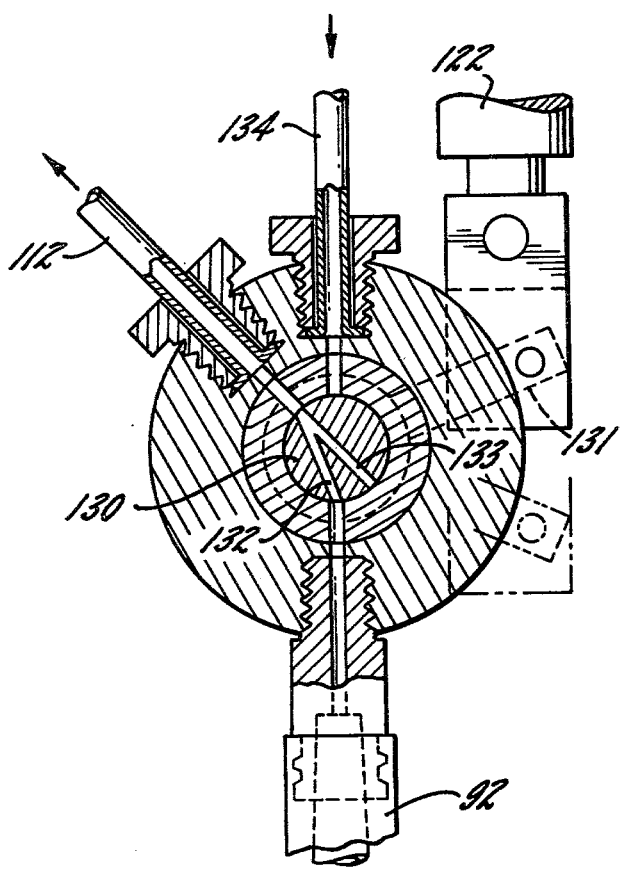
FIG. 7 is an enlarged fragmentary section taken generally along line 7—7 in FIG. 6.

As shown most clearly in FIG. 7, each of the valves V1-V6 includes an internal rotor 130 which is connected by a link 131 to one of the pneumatic cylinders 120-125. When the rotor 130 is in the position illustrated in FIG. 7, the corresponding syringe 92 is connected via internal passageway 132 in the rotor to tne flexible tube 112 leading to the head 21. When the rod of the actuating cylinder 122 is advanced to the position shown in broken lines in FIG. 7, the rotor 130 is turned to connect the syringe 92 through a second internal passageway 133 to a flexible tube 134 leading to the reagent reservoir vial 97.

The vials 95-98 and 140 connected to the valves V1-V6 are housed in cavities formed by a tank 135 containing a precooled eutectic fluid to maintain the temperatures of the liquids therein at a relatively constant temperature, e.g., approximately 4° C. The tank 135 is conveniently mounted on the inside of a door 136 to facilitate replacement or re-filling of the vials 95-98. As illustrated in FIG. 13, the tops of the vials 95-98 are all connected to a dry air manifold 141 to supply air to the head spaces of these reservoirs. Air is not needed in the head space of the vial 140, because this vial simply contains a heat exchanger which is utilized to reduce the temperature of buffer liquid withdrawn from the reservoir 99 before it enters the syringe 94 for eventual discharge to the tube 82 leading to dispenser port 83. The liquid that enters the vial 140 simply passes through a double helical tube 142 within the vial 140 to provide sufficient heat exchange surface to reduce the temperature of that fraction of the buffer liquid to approximately the temperature of the reagents in the other four vials 95-98.

To dispense the four reagents from the syringes 90-93, along with the aspirated liquid samples stored in the tube 82, the valves V1-V5 are turned to the "head" position, and the motor 80 is energized to raise the drive bar 100 and thereby advance the plungers of all six syringes 81 and 90-94. The tubes 110-113 connected to the syringes 90-93 are all prefilled with the respective reagents so that the volumes of these reagents forced into the head 21 are directly proportional to the upward movement of the plungers of the respective syringes. At the same time that the four syringes 90-93 dispense their respective reagents into the head 21, the syringe 94 forces cooled buffer liquid through the tube 14 into tube 82 so as to force the previously aspirated liquid sample out of the tube 82 and into the head 21. Thus, the aspirated liquid sample is dispensed along with the four reagents. During this upward, dispensing stroke of the syringe plungers, the valve V6 connected to the aspirating syringe 81 is in the "reservoir" position so that it simply discharges the buffer liquid that was drawn into the syringe 81 during the aspirating step, back into the buffer reservoir 99. As can be seen most clearly in FIG. 11, all the liquids that enter the head 21 through the tubes 110-113 and 82 are forced downwardly through the central longitudinal bore 21a of the head 21 and are discharged from the tip at the lower end of the head.

In accordance with one specific aspect of the invention, the head 21 is purged with air at the end of each dispensing cycle to remove any remaining liquid from the vertical bore head, so that subsequent aspiration of a liquid sample through the head produces an air pocket between the aspirated sample and the buffer liquid in the storage line 82. Thus, as shown most clearly in FIG. 11, the illustrative dispenser head has a low pressure (e.g., 0.5 psi) air line 150 leading into a cavity 151 at the top of the vertical bore 21a. This air line 150 is normally closed off from the bore 21a by a valve 152 which is held in its lowered position (not shown in FIG. 11) by high pressure air (e.g., 35 psi) from a line 153 acting on a plunger 154. In this closed position, the valve 152 prevents liquids from backing up into the air line 150 during dispensing and aspirating operations.

At the end of each dispensing operation, the supply of pressurized air to the line 153 is turned off so that a spring 15 moves the valve 152 to the upper position shown in FIG. 11. This opens the air line 150 to admit low pressure air into the bore 21a and thereby purge any remaining liquid therefrom. As mentioned previously the resulting void in the bore 21a produces an air pocket between the buffer liquid in line 82 and any liquid sample subsequently aspirated through the head 21 into the line 82. This air pocket is desirable to prevent diffusion of any portion of the aspirated sample into the buffer liquid.

Before initiating operation of the illustrative system, it may be pre-programmed by manual input signals entered on a program panel 160. This panel 160 has a bank of pushbuttons P1-P6 that may be used to select (1) the volumes of reagents to be dispensed from the four syringes (P1-P4); (2) the volume of buffer liquid to be dispensed from the buffer syringe (P5); and/or (3) the volume of any liquid sample to be aspirated and temporarily stored in the system (P6). The liquid volumes selected by operation of these pushbuttons P1-P6 is displayed in digital form in a display window D directly above the pushbuttons.

To select the volumes of reagents and buffer liquid to be dispensed from each of the five syringes 90-94, the operator depresses the five pushbuttons P1-P5 to generate digital electrical signals (proportional to the time interval that each button is depressed) representing the selected volumes. The particular volume selected by the depression of each pushbutton is indicated by the digital display D. These signals are stored in a conventional memory unit for subsequent control of the vertical travel of the drive bar 100 for the syringe plungers. Typically, each increment of change in the digital signal (each integer change in the display D) represents 10% of the available volume of liquid in the corresponding syringe; thus, any one of ten different volumes, 0 through 90%, may be selected for each syringe. Further variations in the liquid volumes may be effected by the use of syringes with different bore sizes, and therefore, different volumes.

When the plunger drive bar 100 is lowered, its downward travel is determined by the maximum volume of reagent, buffer liquid or aspirated sample selected by the operator. That is, the drive bar 100 is lowered a sufficient distance to aspirate the maximum selected volume of reagent, buffer liquid or liquid sample. The drive bar is also preferably lowered by an additional 30% of its total stroke, beyond that needed to aspirate the maximum selected volume of reagent or liquid sample, to permit the dispensing of a 30% volume of buffer liquid to follow the dispensing of the aspirated sample and reagents. This lag in the dispensing of the buffer liquid flushes any remaining sample and/or reagents from the aspirated sample line 82 and the head 21, which is a particularly important feature when dealing with radioactive samples. Of course, if the total amount of buffer liquid selected by the operator is less than a 30% volume, or if the maximum amount of any one reagent or the aspirated sample is greater than a 70% volume, then the amount of buffer liquid that follows the dispensing of the reagents and the aspirated sample must be less than a 30% volume.

During downward movement of the syringe plungers, the valves V1-V5 are all set at the "reservoir" position to draw the respective reagents and buffer liquid from the reservoirs 95-99 into the syringes 90-94. If the system has been programmed to include a sample aspiration step, the valve V6 is set at the "head" position until the selected volume of sample has been aspirated, at which point the valve V6 is switched to the "reservoir" position so that any further retraction of the plunger of the syringe 81 merely draws buffer liquid out of the reservoir 99. This switching of the valve V6 may be effected manually, but is preferably controlled by an electrical signal responsive to (1) a digital electrical signal generated by the "aspirate sample" pushbutton P6 and stored in a memory and (2) a digital electrical signal generated in response to downward movement of the drive bar 100; when these two signals are equal, they indicate that the selected sample volume has been aspirated and, therefore, it is time to switch the valve V6 from the "head" to the "reservoir" position to terminate the sample aspiration.

It will be understood that a number of different means can be employed to sense when the two digital signals are equal and, therefore, when to switch the valve V6. For example, the signals generated in response to the pushbutton P6 and the downward movement of the drive bar 100 may be fed to a conventional electronic comparator which detects when the two input signals are equal and generates an output signal to a solenoid-operated valve controlling actuation of the cylinder 125.

To avoid unnecessary downward movement of the drive bar 100, the drive motor 80 is de-energized when it has lowered the drive platform 100 far enough to aspirate the maximum selected volume of reagent, buffer liquid or liquid sample, plus the additional 30% stroke needed to flush the system with buffer liquid after dispensing of the reagents and aspirated sample has terminated. This de-energization of the motor 80 may be effected manually, but is preferably controlled by an electrical signal responsive to (1) the digital electrical signals generated by the six pushbuttons P1-P6 and (2) a digital electrical signal generated in response to upward movement of the drive bar 100; when these two signals are equal, they indicate that the volumes selected by the six pushbuttons P1-P6 are available in the syringes, and the motor 80 is de-energized to stop the drive bar 100.

When downward movement of the drive bar 100 is terminated, the motor 80 is de-energized just long enough to permit the head 21 to be moved to the selected dispensing position. As the motor 80 is energized in the reverse direction to advance the syringe plungers, the valves V1-V6 associated with the syringes having the maximum settings are switched to the "head" position to initiate the dispensing operation, and the valves associated with lower settings are switched to the "head" position for appropriate intervals during upward movement of the drive bar 100 and the syringe plungers to dispense the selected volumes of reagents, buffer liquid and aspirated sample. This upward movement of the drive bar 100 continues until the plungers of the six syringes have all reached the "zero" level, at which point an actuator 161 carried on the back of the bracket 103 triggers a photoelectric sensor 162 to generate a control signal that de-energizes the motor 80 again. Switching of all the valves V1-V6 at the desired intervals during upward movement of the drive bar 100 may be effected automatically in the same manner described above for the valve V6. Actual movement of the valves V1-V6 is effected by the pneumatic cylinders 120-125 which are controlled either manually or by solenoid-operated air valves controlled by the output signals from electronic comparators receiving input signals responsive to (1) the pushbuttons P1-P6 and (2) upward movement of the drive bar 100.

In order to allow the dispensing of the buffer liquid to trail the dispensing of the reagents and aspirated sample, the valves V1-V4 are preferably switched to the "head" positions and then back to the "reservoir" positions during the initial stages of the upward movement of the syringe plungers. Then the valve V5 remains in the "head" position after all the other valves have been returned to the "reservoir" positions to flush the tube 82 and the head 21.

Figure 14:
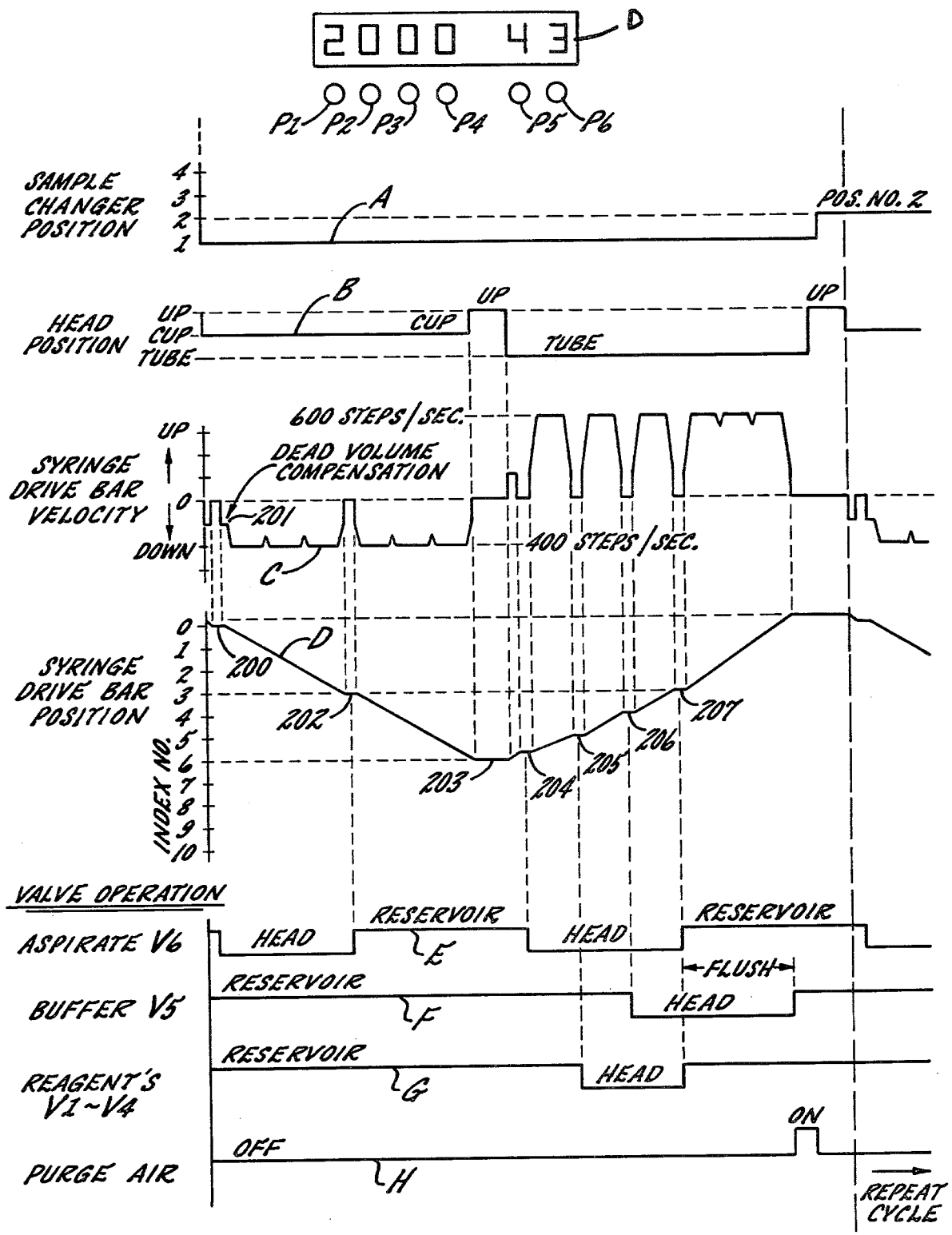
FIG. 14 is a timing diagram illustrating an exemplary operating cycle of a portion of the system embodied in the instrument of FIGS. 1 through 13.

The synchronization of movement of the head 21, the syringe drive bar 100, and the valves V1-V6 can be more clearly understood from the timing diagram in FIG. 14. This timing diagram includes a series of waveforms representing the indexing movement of one of the cassettes 12 along the track 20 (curve A); the position of the head 21 (curve B); the velocity of the syringe drive bar 100 driven by the motor 80 (curve C); the position of the syringe drive bar 100 (curve D); the positions of the valves V6 (curve E), V5 (curve F) and V1-V4 (curve G); and the position of the purge air valve (curve H). As indicated by the digital display D above the pushbuttons P1-P6 at the top of FIG. 14, the exemplary timing diagram is illustrative of a system that has been pre-programmed to dispense a 20% volume of the first reagent (i.e., 20% of the syringe volume), none of the other three reagents and a 40% volume of the buffer liquid and to aspirate and dispense a 30% volume of liquid sample.

Curve A in FIG. 14 simply indicates the time interval during which the first sample tube 10 and specimen cup 11 are in alignment with the dispensing/aspirating head 21. Curve B indicates that the head 21 is initially pivoted to its outboard position in alignment with the specimen cup and lowered into the cup to a depth determined by the position of the limit switch 54. While the head 21 dwells in this position, the motor 80 is energized to lower the syringe drive bar 100 in accordance with the velocity curve C and the position curve D. The positions of the various valves V1-V6 during successive increments of the syringe drive bar movement are illustrated by curves E, F and G. When the syringe drive bar 100 begins its downward movement, all the valves V1-V6 are in the "reservoir" positions so that they are aspirating liquids from the reservoirs 95-99. After the drive bar 100 has moved down only a slight distance, it has stopped momentarily, as indicated by the small flat region 200 in curve D, to allow the valve V6 to be turned to the "head" position. Downward movement of the drive bar 100 is then resumed at its maximum velocity (400 steps/sec. in the example), aspirating a liquid sample from the specimen cup 11.

Because the system has been pre-programmed to aspirate a 30% liquid sample, the valve V6 is maintained in the "head" position until the syringe drive bar 100 reaches index position No. 3 (see curve D), indicating that the syringe plungers have been retracted through 30% of the total stroke length. As can be seen from the velocity curve C, the velocity of downward movement of the drive bar 100 is reduced slightly each time the drive bar reaches one of the index positions so as to allow the downward movement of the drive bar to be quickly stopped at any desired index position. In the illustrative example, the downward movement of the drive bar is immediately resumed at the normal velocity at index positions 1 and 2 and is not stopped until the drive bar reaches index position No. 3, indicating that the desired 30% volume of liquid sample has been aspirated from the specimen cup 11.

It can be seen from curve C in FIG. 14, that the drive bar 100 pauses slightly at an intermediate velocity, indicated by the flat region 201 in curve C, before it reaches its steady state velocity of downward movement toward the first index position. This slight pause at the intermediate velocity causes a slight excess of the liquid sample to be aspirated, in order to compensate for a corresponding increase in the volume of the air pocket that exists in the head 21 when the sample aspiration is initiated. As described earlier, this air void is deliberately produced by purging the head 21 after each dispensing operation, so as to prevent the aspirated liquid sample from coming into contact with the buffer liquid that is withdrawn through the tube 82 in order to effect aspiration of the liquid sample into the head 21. When aspiration of the liquid sample is first initiated, the pressure within this air pocket is reduced slightly, causing the longitudinal dimension of the air pocket to enlarge slightly. If it were not for the compensation provided by the pause at the intermediate velocity 201, the volume of the aspirated sample would be slightly smaller than the volume selected and desired by the instrument operator.

When the syringe drive bar 100 reaches index position No. 3, it is momentarily stopped as indicated by the flat region 202 in the position curve D, to allow time for the valve V6 to be switched to the "reservoir" position. This terminates the aspirating of the liquid sample, and the syringe 81 merely aspirates buffer liquid from the reservoir 99 during subsequent downward movement of the drive bar 100. After the valve V6 has been switched to the "reservoir" position, the downward movement of the drive bar 100 is resumed until it reaches index position No. 6. The downward movement is terminated at index position No. 6 because this provides the stroke length required to dispense the 30% aspirated sample volume plus 30% buffer liquid volume following the dispensing of the aspirated sample for flushing purposes. This will be understood more clearly from the following description of the operation of the valves V1-V6 during upward movement of the syringe drive bar 100.

To provide the time required for the head 21 to be raised out of the specimen cup 11. pivoted to its inboard position in alignment with the sample tube 10, and then lowered into the tube 10, the drive bar 100 dwells at index positions No. 6 for the time interval represented by the flat region 203 in curve D. The drive bar is then raised slightly to compensate for backlash in the drive screw, and then dwells for another short interval represented by the flat region 204 in curve D, during which the valve V6 is turned to the "head" position. Then when upward movement of the drive bar 100 is resumed, the syringe 81 forces buffer liquid through the valve V6 into line 82 to dispense the liquid sample through the head 21.

At this point, it should be recognized that the last three steps of the upward movement of the drive bar 100 should be reserved for dispensing of a 30% volume of the buffer liquid to provide the desired flushing action. That is, it is desirable to complete the dispensing of the selected amounts of reagents, the aspirated samples, and any selected volume of buffer liquid in excess of the 30% flushing volume by the time the drive bar 100 reaches index position No. 3. In the particular example illustrated in FIG. 14, this means that a 20% volume of reagent No. 1, a 30% volume of aspirated sample, and a 10% volume of buffer liquid must be dispensed between index position No. 6 and index position No. 3. As can be seen from curves E, F and G, the aspirated liquid sample is dispensed between index position No. 6 and index position No. 3 (curve E), the 10% volume of buffer liquid is dispensed between index position No. 4 and index position No. 3 (curve F), and the 20% volume of reagent No. 1 is dispensed between index position No. 5 and index position No. 3. To effect the necessary valve functions to initiate the respective dispensing operations at the appropriate index positions the upward movement of the drive bar 100 is momentarily stopped at each of the index positions No. 5, No. 4 and No. 3, as indicated by the flat regions 205, 206 and 207 in curve D. At index position No. 5, valve V1 is turned to the "head" position; at index position No. 4 the valve V5 is turned to the "head" position; and at index position No. 3 the valves V6 and V1 are both returned to the "reservoir" position. The final 30% volume of the buffer liquid is then dispensed through valve V5 as the drive bar 100 traverses the last three index steps, and the valve V5 is finally returned to the "reservoir" position when the drive bar reaches its home position where the actuator 51 triggers the photoelectric sensor 52 to deenergize the drive motor 80. At this point the valve 152 is also opened, by interrupting the supply of high pressure air to the line 153, to admit purging air into the head 21. As indicated by curve H, the valve 152 remains open for only a brief interval, after which the head 21 is raised out of the sample tube 10 (curve B), the next sample tube 10 is indexed into alignment with the head (curve A), and the head is pivoted to its outboard position and lowered into the second specimen cup 11 (curve B). At this point one complete operating cycle has been completed and the system is ready to begin a second cycle.

As can be seen from the foregoing detailed description, this invention provides an improved pipetting system which is capable of dispensing multiple reagents quickly and accurately. It is also capable of aspirating liquid samples from outside the system and then dispensing the aspirated samples along with multiple reagents stored in the pipetting system. This ensures that each aspirated sample is completely discharged from the system before aspiration of the next sample, and it ensures the aspiration and dispensing of accurate preselected volumes of the various liquids. The preselected volumes may also be easily adjusted. To minimize liquid carry-over between receptacles, to avoid liquid splashing within the receptacle, and to accommodate different sizes of sample tubes, the system also permits automatic control of the vertical travel of the dispensing heads.

We claim as our invention:

1. A pipetting system for dispensing multiple liquids into a single receptacle, said system comprising the combination of a plurality of internal liquid reservoirs holding a plurality of different reagents, an internal reservoir of buffer liquid, a plurality of syringes each of which is connected to one of said internal reservoirs for aspirating and dispensing preselected volumes of said reagents and said buffer liquid, a sampling syringe for aspirating a preselected volume of an external liquid sample, a common dispensing/aspirating head connected to all of said syringes for receiving the aspirated sample from an external source and for simultaneously dispensing said sample and said plurality of reagents, a plurality of switchable valves each of which is connected to one of said syringes for selectively connecting said syringes to the respective reservoirs or to said dispensing/aspirating head, and means for switching said valves at preselected positions of the syringes, and means for operating said syringes in unison for simultaneously aspirating said reagents and sample and then simultaneously dispensing said preselected volumes of the reagents and sample.

2. A pipetting system as set forth in claim 1 which includes means for purging said common dispensing head at the end of each dispensing operation to ensure that the entire preselected quantities of liquids are dispensed from said head.

3. A pipetting system as set forth in claim 1 which includes means for adjusting said preselected quantities of liquids.

4. A pipetting system as set forth in claim 1 wherein said dispensing head is mounted for vertical movement to permit the lower end of the head to be lowered into the receptacle into which said liquids are to be dispensed, and including means for automatically stopping the lowering movement of the head at a preselected elevation, and means for adjusting said preselected elevation.

5. A pipetting system as set forth in claim 4 which includes means for automatically stopping upward movement of said dispensing head at a predetermined elevation.

6. A pipetting system as set forth in claim 1 which includes means for flushing said dispensing head with a buffer liquid after at least certain of said preselected quantities of liquids have been dispensed.

7. A pipetting system as set forth in claim 1 which includes means for moving said dispensing head horizontally between dispensing and aspirating positions, aspirating means for withdrawing said external liquid sample from a container into said dispensing head at said aspirating position, and means for storing the aspirated sample while the dispensing head is moved from the aspirating position to the dispensing position.

8. A pipetting system as set forth in claim 7 which includes means for flushing said storage means for the aspirated sample with a buffer liquid after the aspirated sample has been dispensed.

9. A pipetting system as set forth in claim 7 wherein said dispensing head is mounted for vertical movement in both the dispensing and aspirating positions to permit the lower end of the head to be lowered into both the aspirating container and the dispensing receptacle, and including means for automatically stopping the lowering movement of the head at different preselected elevations in said dispensing and aspirating positions, and means for adjusting said preselected elevations.

10. A pipetting system as set forth in claim 7 wherein said aspirating means includes means for aspirating a buffer liquid through a storage line connected to said head and thereby aspirating said liquid sample into said head and storage line, and which includes means for purging said dispensing head with air at the end of each dispensing operation to remove any remaining liquid from said head whereby subsequent aspiration of said liquid sample through said head produces an air pocket separating the aspirated sample from the buffer liquid in said storage line.

11. A pipetting system as set forth in claim 10 which includes means for preselecting the volume of liquid sample to be withdrawn into said dispensing head and storage line, and means for aspirating a volume of liquid sample slightly in excess of the preselected volume to compensate for an increase in the size of said air pocket during the aspiration of said sample.

12. A pipetting system as set forth in claim 1 which includes means for detachably connecting said syringes to said valves and drive means to permit the connection of syringes of different internal volumes in the system.

* * * * *